United States Patent [19]

Exley

[11] Patent Number: 5,559,114
[45] Date of Patent: Sep. 24, 1996

[54] TREATMENT OF AUTOIMMUNE DISEASE USING 2-AMINO PURINE DERIVATIVES

[76] Inventor: Ray W. Exley, 9504 High Ridge Pl., Beverly Hills, Calif. 90210

[21] Appl. No.: 358,335

[22] Filed: Dec. 16, 1994

[51] Int. Cl.$^6$ .................................................. A61K 31/52
[52] U.S. Cl. ........................................ 514/261; 514/262
[58] Field of Search ..................................... 514/261, 262

[56] References Cited

U.S. PATENT DOCUMENTS

| | | | |
|---|---|---|---|
| 4,199,574 | 4/1980 | Schaeffer | 424/200 |
| 4,221,794 | 9/1980 | Simon et al. | 424/253 |
| 4,853,386 | 8/1989 | Friebe et al. | 514/266 |
| 5,059,604 | 10/1991 | Krenitsky et al. | 514/261 |
| 5,075,445 | 12/1991 | Jarvest et al. | 544/276 |
| 5,098,906 | 3/1992 | Sircar et al. | 514/262 |
| 5,246,937 | 9/1993 | Harnden et al. | 514/261 |
| 5,250,688 | 10/1993 | Harnden et al. | 514/277 |

FOREIGN PATENT DOCUMENTS 0077460  4/1983  European Pat. Off. ........ A61K 31/52

OTHER PUBLICATIONS

Adour et al., (1984) "Current Medical Treatment for Facial Palsy" *The American Journal of Otology* 5:499–502.

Baethge et al., (1989) "Case Report: Herpes Zoster Myelitis Occurring During Treatment for Systemic Lupus Erythematosus" *The American Journal of the Medical Sciences* 298:264–266.

Lycke et al., (1989) "Acyclovir Concentrations in Serum and Cerebrospinal Fluid at Steady State" *Journal of Antimicrobial Chemotherapy* 24:947–954.

Shelley et al., (1989) "Essential Progressive Telangiectasia in an Autoimmune Setting: Successful Treatment with Acyclovir" *J. Am. Acad. Dermatol* 21:1094–1096.

Harrison et al., (1993) "Acyclovir in Rheumatoid Arthritis" *The Journal of Rheumatology* 20:761–762.

Feinman et al., (1993) "Central Nervous System Herpesvirus Infection in Systemic Lupus Erythematosus: Diagnosis by Endoretinal Biopsy" *The Journal of Rheumatology* 20:1058–1061.

*Primary Examiner*—Russell Travers
*Attorney, Agent, or Firm*—Cooley Godward Castro Huddleson & Tatum

[57] ABSTRACT

A method for treating autoimmune disease in a mammalian subject, particularly a human, which method comprises administering a therapeutically effective amount of certain 2-amino purine compounds to the subject. The compounds particularly useful are antiviral compounds exemplified by acyclovir, penciclovir and famciclovir. The compounds are administered at doses significantly higher than the dose level used to treat viral infections, e.g., doses that will result in blood plasma levels of about 3–10 micrograms/ml.

15 Claims, No Drawings

TREATMENT OF AUTOIMMUNE DISEASE USING 2-AMINO PURINE DERIVATIVES

FIELD OF THE INVENTION

The present invention relates to the use of 2-amino purine derivatives to treat autoimmune disease(s), particularly the inflammation, tissue destruction caused by the inflammation and the pain of autoimmune diseases and related autoimmune conditions.

BACKGROUND OF THE INVENTION

U.S. Pat. No. 4,199,574 describes a broad class of 6- and 2, 6-substituted purine derivatives containing an acyclic side chain (particularly hydroxyethoxymethyl) in the 9 position that were found to have antiviral activity against various classes of DNA viruses, particularly against herpes viruses such as herpes simplex. Among these derivatives, 9-(2-hydroxyethoxymethyl) guanine (generically known as acyclovir) has been found to have particularly good activity against herpes simplex viruses.

It is also known that a related class of purine derivatives characterized by the presence of a hydrogen atom in the 6 position of the purine nucleus is converted in vivo by the action of the molybdo-flavo-protein enzymes xanthine oxidase/dehydrogenase or aldehyde oxidase into the corresponding 6 hydroxypurine compound acyclovir. The 6-hydrogen compounds are disclosed in U.S. Pat. No. 5,059,604, issued Oct. 22, 1991 to Krenitsky and Beauchamp.

Another compound that is known to be useful for treating the viruses in the herpes simplex family is a compound called famciclovir chemically known as 2-[2-(2-amino-9H-purin-9-yl)ethyl]-1,3-propanediol diacetate. This compound is a prodrug of the antiviral agent penciclovir, which is the corresponding analog of famciclovir where there is a hydroxy at the 6 position in the purine ring instead of a hydrogen. The chemical name of penciclovir is 9-(4-hydroxy-3-hydroxymethyl-1-butyl)guanine. These and related compounds are described in U.S. Pat. Nos. 5,246,937 issued Sep. 21, 1993; 5,250,688 issued Oct. 5, 1993; and 5,075,445 issued Dec. 24, 1991.

The Food and Drug Administration (FDA) currently approves acyclovir and penciclovir for the treatment of vesicle outbreaks of HSV-I and HSV-II. Famciclovir is FDA approved for the treatment of the vesicle outbreak phase of herpes zoster. Such treatment requires blood levels between 0.5 microgram/milliliter (ugm/ml) and 1.0 ugm/ml for acyclovir and similar levels for famciclovir. The currently recognized oral doses required to reach this blood level for an adequate amount of time (which varies according to the virus being treated and is based upon the effective half-life of the drug) for reasonable therapeutic effect are as follows:

1. Famvir® brand famciclovir is only approved for use against Zoster at the oral doses of 500 mg three times per day. The absorption is linear in this dose range.

2. Zovirax® brand acyclovir is approved for several different uses against several different presentations of herpes viruses at oral doses that range between 200 mg three times per day and 800 mg 5 times per day. Because the absorption of acyclovir is non-linear in this dose range Burroughs-Wellcome, the manufacturer, has discouraged the use of higher doses because it believes little more can be absorbed with doses higher than the maximum dose of 800 mg 5 times per day, which in most patients gives a blood level near 1 umg/ml.

Autoimmune disorders are conditions in which the body's immune system produces antibodies to the body's own tissues (i.e., endogenous antigens). This attack on the body is the reason for the names autoimmune and autoantibody. Although, much is known about these diseases, the etiology of all of them is unknown as is the relationship between the various autoimmune disease conditions. It is known that in the most severe cases there is demonstrable antibody to otherwise apparently normal body tissue (i.e., autoantigens). However, there is a large spectrum of autoimmune-associated conditions that frequently occur in patients without demonstrable circulating autoantibodies. These include the myofascial pain syndrome, the irritable bowel syndrome, interstitial cystitis, etc. It is not known to current medical science whether these autoimmune-associated disorders are milder expressions of the same disease processes or totally separate entities. While it is assumed by many researchers in this field that there are causative agents for these conditions, such agents have not heretofore been identified.

At least four possible mechanisms are recognized for developing an immune response to auto-antigens. These are briefly discussed in *The Merck Manual of Diagnosis and Therapy, Sixteenth Edition,* Robert Berkow, M.D., Editor-in-Chief, 1992, Merck Research Laboratories, chap. 20. Many diseases that are thought to belong to this family of disorders are set forth at p. 340 of the Merck Manual. Systemic lupus erythematosus (SLE), rheumatoid arthritis (RA) and systemic sclerosis (scleroderma, old name) are major diseases in this category. In the population afflicted with autoimmune disorders there is autoimmune inflammation, tissue destruction and often a very high level of pain. Frequently these signs and symptoms are so debilitating that a subject is so overcome that he or she can't function normally. Drugs for treating autoimmune diseases such as rheumatoid arthritis are set forth in The Medical Letter on Drugs and Therapeutics, vol. 36 (Issue 935), November 11, 1994. All of the current treatments such as non-steroidal anti-inflammatory agents (NSAIDS), steroids, etc. work by directly interfering with and suppressing the body's immune response. They all are inadequate primarily because of the following problems:

1. The current therapies only slow and diminish but do not arrest the inflammatory process and the progression of the autoimmune disease(s). This is because if they were used in a manner to totally suppress the immune system, the result would be the same as AIDS.

2. They frequently have such severe life threatening side effects that their use must be curtailed in the patient with the most severe autoimmune disease. Thus, the patients who need treatment most critically cannot get adequate control of the autoimmune inflammation before the regimen must be curtailed to prevent serious injury or death from the toxic effects of the medications. The side effects of many recognized treatments are too severe for use in "mild" autoimmune disease(s), the cure is often more dangerous than the disease(s) in these circumstances.

In accordance with this invention, it has now been found, that by administering certain 2-amino purine derivatives (e.g., certain antiviral compounds) at very high dosages, the signs and symptoms, particularly inflammation, tissue destruction and the pain, associated with autoimmune disorders can be ameliorated to the point where a subject can continue functioning in a normal fashion and the tissue destruction is arrested with no dangerous side effects, though with acyclovir there may be severe discomfort.

SUMMARY OF THE INVENTION

One aspect of this invention is a method for treating autoimmune disease in a mammalian subject, particularly one that experiences high levels of inflammation, tissue destruction and/or pain associated with such disease, which method comprises administering a therapeutically effective amount of a compound of Formula (I) of Formula (II) to a subject in need thereof.

Formula (I) is

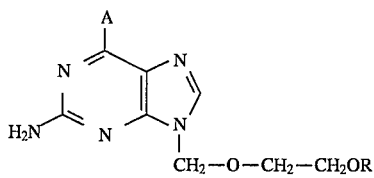

where

A is H or OH and OR is OH or a lower alkyl ester of 2–4 carbon atoms and

Formula (II) is

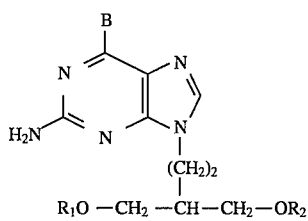

wherein

B is hydrogen, chlorine, alkoxy of 1–6 carbons, phenoxy, phenylalkyloxy, —$NH_2$, —OH or —SH, each of $R_1$ and $R_2$ is independently hydrogen,

or phosphate wherein $R_3$ is an alkyl of 1–6 carbons, alkoxy of 1–6 carbons or optionally substituted aryl; or $R_1$ and $R_2$ are joined together to form a cyclic acetal, a cyclic carbonate or a cyclic phosphate group. The compound is administered in an amount sufficient to provide the level of such compound in the subject's blood plasma to reduce the subject's inflammation, tissue destruction and/or pain.

DETAILED DESCRIPTION OF THE INVENTION

One aspect of the invention is a new method for treating autoimmune disease in a mammalian subject, particularly a human patient who experiences high levels of inflammation, tissue destruction and/or pain associated with such a disease, with a compound of Formula (I) or (II) in an amount sufficient to provide the levels of the compound in the subject's blood plasma to reduce the inflammation, tissue destruction and/or pain level and improve other signs or symptoms. While the mechanism of action is not understood as to how the compounds of the invention work, it has been found by providing a subject with a therapeutically effective amount (i.e., extraordinarily high dosages as compared to the levels approved for antiviral usage) of the compounds of the invention, the inflammation and other signs and symptoms can be reduced, e.g., about 80% with acyclovir and about 90% with famciclovir.

Autoimmune disease is meant to encompass those conditions in which the body's immune system produces antibodies to the body's own tissue (i.e., endogenous antigens). Generally the conditions are associated with inflammation, tissue destruction and pain. Many conditions are included under the autoimmune disease "umbrella" and are set out in the Merck Manual at Chapter 20 and elsewhere. Major diseases include SLE, RA and systemic sclerosis. The latter may occur with or without autoimmune renal destruction and autoimmune associated conditions including but not limited to irritable bowel syndrome, tic douloureux (trigeminal neuralgia), myofascial pain syndrome, interstitial cystitis, Reiter's syndrome, and the like. Also included is multiple sclerosis and chronic non-cancer pain. While some clinicians may consider chronic non-cancer pain as a distinct, unrelated entity, it is included here with the view that it is another manifestation of autoimmune disease. Sometimes it may be considered as myofascial pain syndrome or trigger point syndrome.

Patients with autoimmune disease often suffer significant inflammation of the kidneys, often causing renal destruction. The best clinical laboratory measure of kidney function is creatinine clearance. In many cases the kidney function is so reduced that death results. In addition, a significant pain level is often experienced. The pain can be in the joints and the muscles of the back, the esophagus and the bowels. The pain level may come and go in spasms which reduces the normal functioning of an individual. Other symptoms that are seen in the autoimmune patients (e.g., rheumatoid arthritis) include the inflammation and tissue destruction of the joints; When this occurs in the hands, the swelling and tissue destruction is sometimes so great that the hands cannot be closed. Another frequent sign in patients with autoimmune disease is the appearance of a "butterfly" rash across the face, particularly in SLE.

While the cause(s) of autoimmune diseases or conditions is/are not known, it is believed that there is/are causative agent(s). The current belief is that each individual condition or disease that is included under the umbrella of "autoimmune disease" probably has a different causative factor or etiology. While not wishing to be bound by any theory of operation of the method of this invention, Applicant's invention is based, at least in part, on the concept that each of the individual conditions or diseases included under the classification of autoimmune disease is caused by one or more members of the herpes virus family. Thus the invention is based upon an entirely different approach to the problem of treating autoimmune disease(s). This technique is based upon an attempt to stop the production of the antigens stimulating the autoimmune attack. Under the current theory the immune system is behaving abnormally by attacking normal cells and intracellular membranes. The method of this invention is predicated upon the theory that the normal appearing cells (normal to our current technologies) are infected with viral DNA and are producing viral proteins. These viral proteins are "foreign" to the immune system and thus it initiates attack upon them. This results in an "adjuvant effect" for the cell membranes. Thus the immune system begins to attack the normal cell membranes of the nucleus, the mitochondria, the cell wall or other cellular components causing inflammation and tissue destruction. The theory predicts that is the underlying production of "foreign proteins" is suppressed, there will be no longer "adjuvant" stimulation. Then the immune system may diminish or cease it's attack upon the normal membranes.

Of all the viruses that have widespread distributions in the human population, the herpes viruses display the most aggressive long term continued testing of the immune system. When the immune system fails or is suppressed a new presentation of the herpetic vesicle phase commonly results. This is not true for measles, and numerous other common viral illnesses. Herpes displays a preference for and an ability to survive in nervous tissue for long periods. Many of the symptoms of autoimmune associated conditions could be explained by limited focal irritation of the sympathetic nervous system. Herpes viruses display the ability to erupt focally in zoster (shingles) and HSV-I and HSV-II. This and other characteristics of this family of viruses make them "the likely suspects."

The herpes family includes Varicella-Zoster (chicken pox-shingles), HSV-I, HSV-II, cytomegalovirus, Epstein-barr virus and several others that infect humans. Animals suffer diseases from this family including Marek's disease in fowl and pseudo-rabies in dogs, cats and cattle. Belief that the herpes virus can cause autoimmune diseases is consistent with the known behavior of the viruses in immune-suppressed individuals. Most children are infected within 5 years of birth and suffer a short episode of varicella (chicken pox). The immune system then suppresses the infection, which then becomes latent only to reexpress itself after the age of 50 as shingles, usually very localized presentation involving only one, two or three nerves. This expression almost inevitably occurs in immunosuppressed patients, such as AIDS or transplant patients. HSV-II infects about 25% of all people in the U.S. It also represents in immunosuppressed patients, as the viral shedding vesicle eruptions. Thus, the expression of the most dramatic viral shedding stage of the virus is held in check by the immune system.

Patients with known autoimmune disease(s) or related conditions who have herpetic outbreaks are frequently placed upon the currently approved doses of acyclovir to treat the viral infection. While some report improvement in their subjective feelings regarding the symptoms of autoimmune disease, in several controlled studies the observers reported no difference between treated and control patients. Burroughs-Wellcome, the manufacturer of acyclovir strongly discourages the use of higher doses by claiming that because poor solubility of acyclovir, no more than the amount absorbed from a single 800 mg dose administered every six hours (q6h) can be absorbed. The applicant proved that significantly higher blood levels than 1 ugm/ml (the currently approved desirable level) can be achieved in humans for acyclovir if enough is given to overcome the nonlinear solubility. These higher levels have been shown to be effective for treating autoimmune disease. Blood acyclovir levels of, e.g., over 6.5 ugm/ml have been repeatedly measured. Since the famciclovir dose response is linear in this range, relatively lower doses than acyclovir may accomplish adequate blood levels to suppress the production of "foreign" herpetic proteins.

One of the unique aspects of the method of this invention is the effect on the kidneys, as measured by creatinine clearance. It is generally believed that once kidney function has been significantly reduced, for example by inflammation, it will not return to normal. However, in the method of this invention, it has been discovered that kidney function that was significantly reduced by the autoimmune processes (e.g., creatinine clearance reduced from a normal of about 120 ml/min down to about 30 ml/min) could be improved by administering a compound of Formula (I) (acyclovir) or (II) (famciclovir) (e.g., up to about 60 ml/min from 30 ml/min). This phenomenon has previously been unreported. Presumably, this very significant return of kidney function is due to the many glomeruli being simultaneously in various stages of autoimmune inflammation and destruction. Some of the glomeruli may be destroyed beyond return of normal functioning, because the clearance did not return to normal. (Also, pathologic examination of typical kidneys from autoimmune disease patients show glomeruli in various stages of inflammation of destruction, with the destroyed being more frequent in patients with less renal function.) Presumably, some of the glomeruli may be inflamed to the point of limited or not functioning, but are then able to resume more normal functioning when their inflammation subsided after 6 months of treatment with effective doses. This is objective evidence that this technique is superior to all previous therapies. It doesn't just slow the inevitable progression of autoimmune diseases, it stops the inflammation and allows damaged and not destroyed tissue to repair itself with return of normal function. As the measured kidney function improved a parallel process occurred with a diminution of the visible inflammation, swelling, pain, grinding and clicks in the afflicted articular joints. Renal function tests that evaluate the severity of reduced kidney function can be found in *The Merck Manual of Diagnosis and Therapy*, Sixteenth Edition, Robert Berkow, M.D. Editor-In-Chief, 1992, Merck Research Laboratories at pp. 1654–1661.

The compounds that are useful for treating autoimmune diseases in accordance with this invention include those of Formula (I) and (II) below.

Formula (I) is as follows:

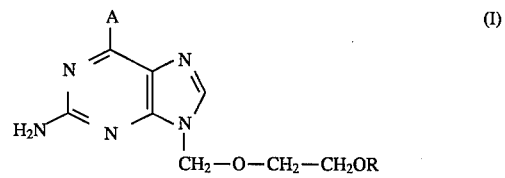

where

A is H or OH and

OR is OH or a lower alkyl ester of 2–4 carbon atoms. Representative lower alkyl esters include the acetate, propionate and butyrate esters. Of these the acetate is preferred. The compound that is particularly useful is acyclovir, where A is OH and R is H (which is disclosed in U.S. Pat. No. 4,199,574 issued Apr. 22, 1980 and which is incorporated herein by reference). It should be noted that for both Formulae (I) and (II) where A or B is designated as OH, an alternative representation of the purine ring would be as follows:

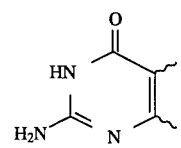

Formula (I) is as follows:

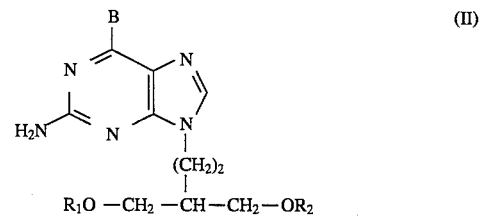

wherein

B is hydrogen, chlorine, alkoxy of 1–6 carbons, phenoxy, phenylalkyloxy, —$NH_2$, —OH or —SH, each of $R_1$ and $R_2$ is independently hydrogen,

or phosphate wherein $R_3$ is an alkyl of 1–6 carbons, alkoxy of 1–6 carbons or optionally substituted aryl; or $R_1$ and $R_2$ are joined together to form a cyclic acetal, a cyclic carbonate or a cyclic phosphate group.

The preferred compounds of formula (II) are those wherein B is hydrogen, OH or alkoxy of 1–6 carbons (particularly hydrogen or OH) and each of $R_1$ and $R_2$ is independently hydrogen or

where $R_3$ is alkyl of 1–6 carbons (e.g., acetyl).

Penciclovir and famciclovir are preferred individual compounds.

For purposes of this patent application the following definitions are applicable:

Alkyl of 1–6 carbons is a branched or straight chain hydrocarbon of 1 to 6 carbon atoms represented, e.g., by methyl, ethyl, n-propyl, i-propyl, n-butyl, t-butyl, 1,1-dimethyl-n-propyl, 3-hexyl, and the like.

Alkoxy of 1–6 carbons is a branched or straight chain alkyl attached to an oxygen, i.e., represented by the formula RO where R is a straight or branched chain alkyl of 1–6 carbon atoms. Representative alkoxy moieties include methoxy, ethoxy, n-propoxy, i-propoxy, n-butoxy, t-butoxy, hexyloxy, and the like.

Aryl includes phenyl which may be optionally substituted with one or two groups selected from alkyl of one to six carbon atoms, alkoxy of one to six carbon atoms or halo such as fluoro or chloro.

In the case of compounds of Formula (II) wherein one of $R_1$ or $R_2$ is an acyl or phosphate group, the compound exists in two enantiomeric forms. The compounds useful in this invention include both an enantiomeres in isolated form and mixtures thereof.

The compounds useful in this invention may be in crystalline form or as a hydrate, and it is intended that both forms are encompassed by the compounds represented by formula (II) above. Examples of pharmaceutically acceptable salts of the compounds of formula (II) are acid addition salts formed with a pharmaceutically acceptable acid such as hydrochloric acid, orthophosphoric acid and sulfuric acid.

When the compound of formula (II) contains a phosphate group suitable salts include metal salts, such as aluminum, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tri-(2-hydroxyethyl)-amine.

Suitable compounds of Formula (II) include;

2-amino-9-(4-hydroxy-3-hydroxymethylbut-1-yl)purine;

2-amino-9-(4-acetoxy-3-hydroxymethylbut-1-yl)purine;

2-amino-9-(4-acetoxy-3-acetoxymethylbut-1-yl)purine;

2-amino-9-(3-hydroxymethyl-4-methoxycarbonyloxybut-1-yl)purine;

2-amino-9-[2-(2,2-dimethyl-1,3-dioxan-5-yl)ethyl]purine;

2-amino-9-(4-propionyloxy-3-propionyloxymethylbut-1-yl) purine;

2-amino-9-(4-butyryloxy-3-hydroxymethylbut-1-yl)purine;

2-amino-9-(4-benzoyloxy-3-hydroxymethylbut-1-yl)purine;

2-amino-9-(4-hydroxy-3-hydroxymethylbut-1-yl)purine 4'-phosphate;

2-amino-9-(4-hydroxy-3-hydroxymethylbut-1-yl)purine 4':4"phosphate;

and pharmaceutically acceptable salts thereof.

The compounds of Formula (II), above are prepared in accordance with the procedures set forth in U.S. Pat. Nos. 5,250,688 issued Oct. 5, 1993; 5,246,937, issued Sep. 21, 1993 and 5,075,445 issued Dec. 24, 1991, all of which patents are incorporated herein by reference.

Generally the compounds may be administered orally, intramuscularly (IM), intravenously (IV) or parenterally, but because of the ease of oral administration the oral route is preferred. A composition which may be administered by the oral route to humans may be compounded in the form of a syrup, tablet or capsule. When the composition is in the form of a tablet, any pharmaceutical carrier suitable for formulating such solid compositions may be used, for example magnesium stearate, starch, lactose, glucose, rice, flour and chalk. The composition may also be in the form of an ingestible capsule, for example of gelatin, to contain the compound, or in the form of a syrup, a solution or a suspension. Suitable liquid pharmaceutical carriers include ethyl alcohol, glycerine, saline and water to which flavoring or coloring agents may be added to form syrups. The compounds may also be presented with a sterile liquid carrier for injection. In general suitable pharmaceutical carriers and methods of preparation can be found in *Remington's Pharmaceutical Sciences*, 18th Edition.

Very high doses of compounds of Formulae (I) and (II) are needed to provide a therapeutically-effective amount of the compounds. By administering the compounds of this invention at such levels, relief is seen of the signs and symptoms associated with autoimmune diseases. For example, the level of pain is reduced significantly, the swelling in the joints and the hands decreases, the butterfly rash is ameliorated and skin pain that might be related is also reduced. It is also been found in a patent with markedly reduced kidney function (as measured by creatinine clearance in ml/min) that prolonged treatment with these agents doubled the creatine clearance from about 30 to 60 ml/min. While any of the compounds encompassed within the generic Formulae of this invention can be used for treating the disease, generally, acyclovir, penciclovir and famciclovir are preferred. Famciclovir is particularly. preferred because it is more water soluble at body pH of 7.4 than other representative compounds such as acyclovir. The rate and frequency of dosing depends on the extent of the autoimmune conditions, individual tolerance and the particular drug chosen for administration. Generally a therapeutically effective amount is a dosage that is very high (i.e., about five to ten times higher) relative to the levels effective for the treatment of conditions due to HSV such as HSV I or II or VZV. The therapeutically effective amount administered is sufficient to give the desired blood levels and ultimately the reduction of the signs and symptoms of the condition. The blood levels may vary from individual to individual but generally need to be between about 3 micrograms per ml to about 10 micrograms per ml, depending on the compound chosen. To achieve such a blood level, an amount administered on a daily basis will vary between about 4 grams per day to about 64 grams per day, although more or less may be administered depending on the activity and bioavailability of the particular compound administered.

In general the compounds are administered at times throughout a day to maintain a blood level that will continue to ameliorate the autoimmune conditions and provide relief to the individual from the symptoms. Thus the dosing may be equal amounts provided 3 or up to 8 times a day depending on the individual and the compound chosen. Preferably the dosing is 5 to 6 times a day.

In administering acyclovir, the material is administered at a rate of about 20 grams per day to about 64 grams per day, preferably no more than about 50 grams/day. Generally, it is administered in four to six equal dosages a day taken throughout the day. This amount is needed because acyclovir is less soluble than penciclovir or famciclovir. The amount of famciclovir which is administered is about 4 grams to about 10 grams a day. Preferably it will be about four to seven and one-half grams per day, delivered about 4 to 6 times a day. The doses discussed in this application are all oral dosing. Parenteral dosing would be adjusted to achieve the desirable blood levels of between 4.5 ugm/ml and 10 ugm/ml. When attempts are made to raise the blood peak levels of acyclovir above, e.g., about 3 ugm/ml into the therapeutic range, there appears to be a transient irritation of all of the inflamed tissues during the rising phase of the dosage roughly between 10 and 30 minutes post intake. The amount of this increase is a function of the degree of underlying inflammation and is greatest in previously untreated patients. The tissue most affected are the nerves of the sympathetic chain. Of the numerous nerves in the sympathetic chain this irritation effect is most marked and problematic on the nerves that send pain signals to the brain and maintain bowel muscle tension. During this "irritation phase" the intensity of the underlying pain or bowel spasm increases about 25% for the duration of 20 minutes. This means that the most effective blood levels may not be achieved initially in previously untreated patients, due to the increased pain. The technique developed for acyclovir is to start a patient at doses roughly 4 times the present FDA-approved maximum dose 5 times per day. Then encourage the patient to "titrate to tolerance". The patient starts with four 800 mg tablets 5 times per day. After one week the dose is increased 1 tablet (800 mg) per dose and continued if tolerated. If not tolerated during the "irritation phase" the dose is dropped back for 1 week then the incremental increase is tried again. When the patient can tolerate the dose it is continued at that level for 1 week and then a higher does is attempted. While end point may vary from patient-to-patient, in one example the patient had a peak blood level around 6.5 ugm/ml. It is expected that some patients may not be able to increase their doses for several weeks at a time. A wide amount of individual variation is expected depending upon many factors such as the localization of the areas of most severe pain, individual tolerance for pain, the determination of the patient to move into an effective therapeutic range and finally the amount of help provided to the patient in emotional support and pain relieving drugs. Without narcotic assistance, the patients can expect this process to take up to six months, sometimes with minimal detectable relief in the underlying symptoms. During this time the "irritation phase" will include signs of severe sympathetic chain irritation such as precipitous bowel evacuations with every dose for patients with irritable bowel syndrome, the same will occur in patients with interstitial cystitis and all will have marked night sweats and exacerbation of "trigger points". After months of therapy and the underlying inflammation is diminished markedly, this irritation phase diminishes accordingly. Famciclovir exhibits a similar irritation effect, but at an intensity only about 20% of acyclovir, and thus is preferred. The "titration to tolerance" for famciclovir is started at 1 gm (2×500 mg tabs) at 5 times per day. It is increased 500 mg (one tablet) per dose after 2 weeks. After 2 more weeks this is repeated. An adequate oral dose appears to be 2 gms (4×500 mg tabs) 5 times per day. As with acyclovir the increases are withdrawn for 1 week if not tolerated because of the "irritation effect", then the increases are retried until tolerated. "Titrating to tolerance" is much easier with famciclovir than acyclovir.

The following examples are given by way of representation of specific administration modes, but should not be interpreted as limiting the scope of the claims in any way.

EXAMPLE 1

This example sets forth the treatment of a patient with severe autoimmune disease signs and symptoms using high doses of acyclovir.

A patient showing significant symptoms of autoimmune disease for about 15 years volunteered for treatment. Records confirmed the original diagnosis was made with the patient's anti nuclear antibodies (ANAs) at titers greater than 1 to 16 million and anti mitochondrial antibodies (AMAs) at titers greater than 1 to 4 million. The patient's creatinine clearance had dropped from a normal level of about 120 ml per minute to about 29 ml per minute. The patient showed moderate joint inflammation with pain, swelling, grinding and clicks in the hands and knees primarily. The patient also had severe myofascial pain and severe irritable bowel syndrome. In addition the patient was diagnosed as having HSV II. The signs and symptoms had developed to such an extent that the patient was unable to work and had very little sleep due to the excessive chronic, unremitting pain caused by the disease condition. After treatment with high dosage of acyclovir in accordance with the method of this invention the patient found that the pain and inflammation was significantly reduced about 90% to the point where he again could sleep and function at a nearly normal rate.

The initial treatment started with about 5 times the currently recommended maximum oral dosage acyclovir, with the initial dosage levels were about 4 grams which equated to twenty 200 gram capsules taken at one time. After three weeks of 20 capsules every six hours, the dosage eventually increased to a level of thirty 200 g capsules every six hours. At about the third week the patient developed over a four to six hour period a gradual but approximately 80% diminution in the previously chronic unremitting pain and spasm in the right T9 paraspinous muscle region. In addition over the first 3 weeks of the treatment the patient noticed a marked diminution in the tenderness and clicking of the joints in the hands and feet. In addition the faint butterfly mask on his face diminished noticeably but would come back fairly quickly if he failed to take a dose at intervals longer than every six hours. Diminution of the "butterfly mask" of autoimmune disease in response to medication has not been previously reported. In this case the "butterfly mask" fluctuates inversely with the blood level of the drug administered. The dosage increased and a side effect after the patient was taking approximately 300 capsules per day, about 50 every six hours, was that he lost his ability to taste salt, sweet, etc. After continuation for six months and at even higher doses, the ability to taste did return to normal. In addition, the patient noticed a thickening of the hair, particularly on the face and head. During this time, the pain reduced to such an extent that the patient could get two and a half to three hours sleep and at sometimes up to four and a half hours sleep without being awakened by the return of significant pain as drug levels fell every 4 hours post dosage.

The patient continued on dosing of acyclovir and found that the signs and symptoms could be reduced about 80% controlled by continued dosing at a rate of about ten 800 mg. tablets (8 grams) 5 to 6 times a day. Higher doses of acyclovir did not cause further decreasing in signs or symptoms.

EXAMPLE 2

This example sets forth the continued treatment of the patient described in Example 1. After three years on acyclovir in higher doses described in Exhibit 1, it was discontinued and famciclovir was started at the rate of about 2 grams 5 to 6 times a day. This is significantly less drug than was provided in Example 1. It is thought that less drug is needed than in Example 1 because famciclovir is more water soluble at body pH than acyclovir. By continued administration of the famciclovir at this level, the symptoms, including the pain and inflammation are controlled to be about 80–90% (as judged subjectively by the patient) of the original levels. It is found that if the dosage is eliminated, the signs and symptoms return to intolerable levels within about 12 hours.

Further aspects of this invention may be apparent to those of skill in the art upon further contemplation of this disclosure.

The subject matter claimed is:

1. A method of treating autoimmune disease in a mammalian subject, which method comprises administering a therapeutically effective mount of a compound of Formula (I) or (II) to a subject in need thereof, wherein (a) Formula (I)

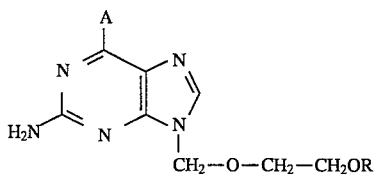

wherein

A is H or OH, OR is OH or a lower alkyl ester of 2–4 carbon atoms and (b) Formula (II) is

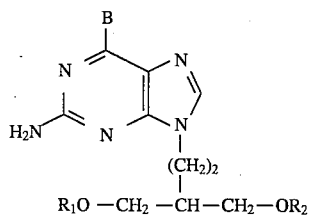

wherein

B is hydrogen, chlorine, alkoxy of 1–6 carbons, phenoxy, phenylalkyloxy, —NH$_2$, —OH— or — SH, each of R$_1$ and R$_2$ is independently hydrogen,

or phosphate wherein

R$_3$ is an alkyl of 1–6 carbons, alkoxy of 1–6 carbons or optionally substituted aryl; or R$_1$ and R$_2$ are joined together to form a cyclic acetal, a cyclic carbonate or a cyclic phosphate group.

2. The method of claim 1 wherein the amount of the compound administered is sufficient to raise the subject's blood plasma levels of the compound to about 3 µg/ml to about 10 µg/ml.

3. The method of claim 2 wherein the compound is represented by Formula (I) where A is H or OH and R is H or acetyl.

4. The method of claim 3 wherein the compound is acyclovir.

5. The method of claim 4 wherein the level of acyclovir in the subject's blood plasma is about 4 µg/ml to about 10 µg/ml.

6. The method of claim 1 wherein the compound is represented by Formula (II) where B is H or OH and each of R$_1$ and R$_2$ is independently chosen from H or acetyl.

7. The method of claim 6 where in the compound is famciclovir.

8. The method of claim 7 wherein the famciclovir is administered in an amount sufficient to give a blood plasma level of about 3.5 µg/ml to about 10 µg/ml.

9. The method of claim 1 wherein the compound is administered orally.

10. The method of claim 9 wherein the compound is acyclovir and is administered at a rate of about 20 grams to about 50 grams per day.

11. The method of claim 9 wherein the compound is famciclovir and is administered at a rate of about 4 grams to about 10 grams per day.

12. The method of claim 1 wherein the autoimmune disease is systemic lupus erythematosus, rheumatoid arthritis, or systemic sclerosis.

13. The method of claim 1, wherein the level of pain associated with the autoimmune disease and experienced by the subject is such that the patient is unable to function normally.

14. The method of claim 1 wherein the subject's kidney function has been significantly reduced below normal creatinine clearance levels.

15. The method of claim 1 wherein the disease is chronic non-cancer pain.

* * * * *